United States Patent
Yoshida (10) Patent No.: US 10,622,398 B2
(45) Date of Patent: Apr. 14, 2020

(54) IMAGE PICKUP APPARATUS AND ENDOSCOPE COMPRISING A GUARD RING FORMED ALONG AN OUTER EDGE ON A WIRE LAYER AND A THROUGH-HOLE WITH AN ELECTRODE PAD HAVING OUTER PERIPHERY PORTION IN CONTACT WITH A SILICON LAYER OVER A WHOLE PERIPHERY

(71) Applicant: OLYMPUS CORPORATION, Tokyo (JP)

(72) Inventor: Kazuhiro Yoshida, Okaya (JP)

(73) Assignee: OLYMPUS CORPORATION, Tokyo (JP)

( * ) Notice: Subject to any disclaimer, the term of this patent is extended or adjusted under 35 U.S.C. 154(b) by 401 days.

(21) Appl. No.: 15/652,833

(22) Filed: Jul. 18, 2017

(65) Prior Publication Data

US 2017/0317130 A1 Nov. 2, 2017

Related U.S. Application Data

(63) Continuation of application No. PCT/JP2015/051885, filed on Jan. 23, 2015.

(51) Int. Cl.
*H01L 27/146* (2006.01)
*A61B 1/00* (2006.01)
(Continued)

(52) U.S. Cl.
CPC ........ *H01L 27/14636* (2013.01); *A61B 1/005* (2013.01); *A61B 1/0011* (2013.01);
(Continued)

(58) Field of Classification Search
CPC ....... A61B 1/0011; A61B 1/005; A61B 1/051; H01L 23/58; H01L 27/14636; H01L 27/14643
(Continued)

(56) References Cited

U.S. PATENT DOCUMENTS 6,756,675 B1 * 6/2004 Tanaka .................... H01L 24/03
257/758
2010/0109006 A1 5/2010 Kobayashi et al.
(Continued)

FOREIGN PATENT DOCUMENTS

JP 2005-209677 A 8/2005
JP 2005-285814 A 10/2005
(Continued)

OTHER PUBLICATIONS

International Search Report dated Apr. 21, 2015 issued in PCT/JP2015/051885.

*Primary Examiner* — Que Tan Le
(74) *Attorney, Agent, or Firm* — Scully, Scott, Murphy & Presser, P.C.

(57) ABSTRACT

An image pickup apparatus includes a silicon layer, a wire layer that contains an insulator having a lower dielectric constant than silicon oxide, a cover glass that covers a light receiving portion on a light receiving surface of the silicon layer, and a silicon substrate that covers a back surface of the wire layer, in which a guard ring is formed along an outer edge on the wire layer, a through-hole having a bottom surface that is configured by an electrode pad configured by a conductor of the wire layer and having an outer periphery portion in contact with the silicon layer over a whole periphery is provided in a region of the silicon layer that is not covered with the cover glass, and the insulator of the wire layer is not exposed to an inner surface of the through-hole.

9 Claims, 7 Drawing Sheets (51) Int. Cl.
*A61B 1/005* (2006.01)
*A61B 1/05* (2006.01)
(52) U.S. Cl.
CPC ...... *A61B 1/00114* (2013.01); *A61B 1/00124* (2013.01); *A61B 1/051* (2013.01); *H01L 27/14618* (2013.01); *H01L 27/14643* (2013.01)
(58) Field of Classification Search
USPC .................................. 250/208.1, 214 R, 239
See application file for complete search history.

(56) References Cited

U.S. PATENT DOCUMENTS

2013/0105667 A1    5/2013    Kobayashi
2013/0105924 A1    5/2013    Kobayashi et al.

FOREIGN PATENT DOCUMENTS

| | | |
|---|---|---|
| JP | 2005-347707 A | 12/2005 |
| JP | 2006-147626 A | 6/2006 |
| JP | 2008-258201 A | 10/2008 |
| JP | 2010-109137 A | 5/2010 |
| JP | 2011-054637 A | 3/2011 |
| JP | 2012-028359 A | 2/2012 |
| JP | 2012-033878 A | 2/2012 |
| JP | 2012-033894 A | 2/2012 |
| JP | 2012-099742 A | 5/2012 |
| JP | 2014-230083 A | 12/2014 |
| WO | WO 2012/001915 A1 | 1/2012 |
| WO | WO 2012/001935 A1 | 1/2012 |
| WO | WO 2014/188788 A1 | 11/2014 |

\* cited by examiner

IMAGE PICKUP APPARATUS AND ENDOSCOPE COMPRISING A GUARD RING FORMED ALONG AN OUTER EDGE ON A WIRE LAYER AND A THROUGH-HOLE WITH AN ELECTRODE PAD HAVING OUTER PERIPHERY PORTION IN CONTACT WITH A SILICON LAYER OVER A WHOLE PERIPHERY

CROSS REFERENCE TO RELATED APPLICATION

This application is a continuation application of PCT/JP2015/051885 filed on Jan. 23, 2015, the entire contents of which are incorporated herein by this reference.

BACKGROUND OF THE INVENTION

1. Field of the Invention

The present invention relates to an image pickup apparatus including a silicon layer on which a light receiving portion is formed, a wire layer that is disposed on the silicon layer and that includes a plurality of conductor layers and a plurality of insulating layers containing an insulating material having a lower dielectric constant than silicon oxide, and a cover glass that is attached so as to cover the wire layer, and an endoscope including the image pickup apparatus.

2. Description of the Related Art

A backside illumination (BSI) type image pickup apparatus, in which a light receiving portion configured by a CMOS image pickup device and the like is formed on a principal surface, has been widely used in endoscopes and the like, because of a small diameter and a high sensitivity. In the image pickup apparatus, a wire layer in which a plurality of conductor layers and a plurality of insulating layers are laminated is essential to obtain a consistency between a light receiving portion that has a fine pattern made by a semiconductor technology and a large bonding electrode to which a signal cable or the like is connected. When a through-hole and the like are formed in the wire layer, an insulating material of the insulating layer is exposed to a bottom of the through-hole.

In recent years, use of a material having a lower relative dielectric constant k than silicon oxide, a so-called Low-k material, for the insulating layer of the wire layer has been studied for enhancing performance of the image pickup apparatus.

Note that Japanese Patent Application Laid-Open Publication No. 2012-28359 discloses a semiconductor apparatus in which a through-hole is formed on a semiconductor substrate to which a glass substrate is attached through an adhesive agent, by an etching from a back surface, and a wire is disposed in the through-hole.

SUMMARY OF THE INVENTION

An image pickup apparatus in an embodiment is an image pickup apparatus including: a silicon layer that includes a light receiving surface and a facing surface, the light receiving surface being a surface that light received by a light receiving portion enters; a wire layer that is disposed on the facing surface, the wire layer including a plurality of conductor layers and a plurality of insulating layers, each of the plurality of conductor layers containing a conductor that is connected to the light receiving portion, each of the plurality of insulating layers containing an insulator that has a lower dielectric constant than silicon oxide; a transparent member that covers the light receiving portion on the light receiving surface of the silicon layer; and a protective portion that covers a back surface of the wire layer, the back surface being a surface on an opposite side of the silicon layer, in which a guard ring is formed along an outer edge on the wire layer, a through-hole is provided in a region of the silicon layer that is not covered with the transparent member, the through-hole having a bottom surface that is configured by an electrode pad, the electrode pad being configured by at least one of the conductors of the conductor layers and having an outer periphery portion in contact with the silicon layer over a whole periphery, and the insulators having the lower dielectric constant of the insulating layers are not exposed to an inner surface of the through-hole.

An endoscope in another embodiment includes, at a distal end portion of an insertion portion, an image pickup apparatus including: a silicon layer that includes a light receiving surface and a facing surface, the light receiving surface being a surface that light received by a light receiving portion enters; a wire layer that is disposed on the facing surface, the wire layer including a plurality of conductor layers and a plurality of insulating layers, each of the plurality of conductor layers containing a conductor that is connected to the light receiving portion, each of the plurality of insulating layers containing an insulator that has a lower dielectric constant than silicon oxide; a transparent member that covers the light receiving portion on the light receiving surface of the silicon layer; and a protective portion that covers a back surface of the wire layer, the back surface being a surface on an opposite side of the silicon layer, in which a guard ring is formed along an outer edge on the wire layer, a through-hole is provided in a region of the silicon layer that is not covered with the transparent member, the through-hole having a bottom surface that is configured by an electrode pad, the electrode pad being configured by at least one of the conductors of the conductor layers and having an outer periphery portion in contact with the silicon layer over a whole periphery, and the insulators having the lower dielectric constant of the insulating layers are not exposed to an inner surface of the through-hole.

DETAILED DESCRIPTION OF THE PREFERRED EMBODIMENTS

First Embodiment

Figure 1:
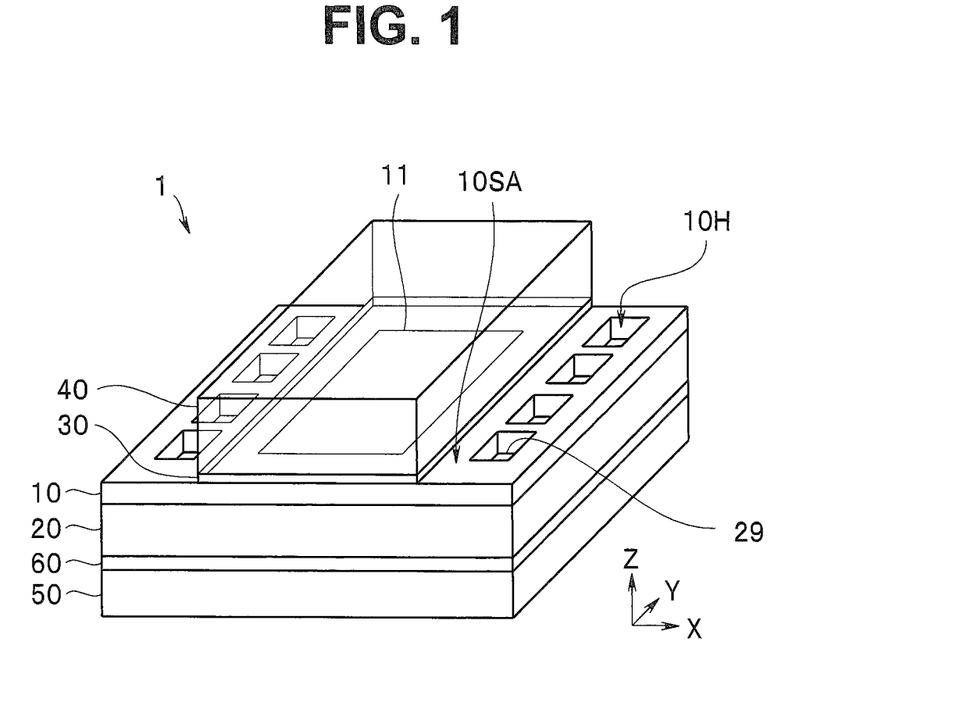
FIG. 1 is a perspective view of an image pickup apparatus in a first embodiment.
Figure 2:
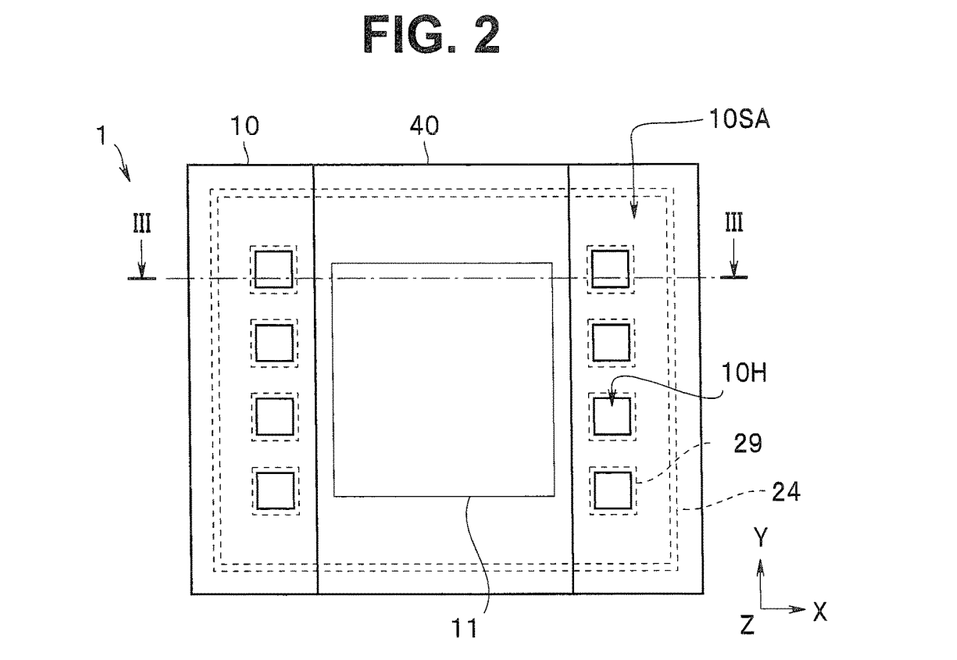
FIG. 2 is a top view of the image pickup apparatus in the first embodiment.
Figure 3:
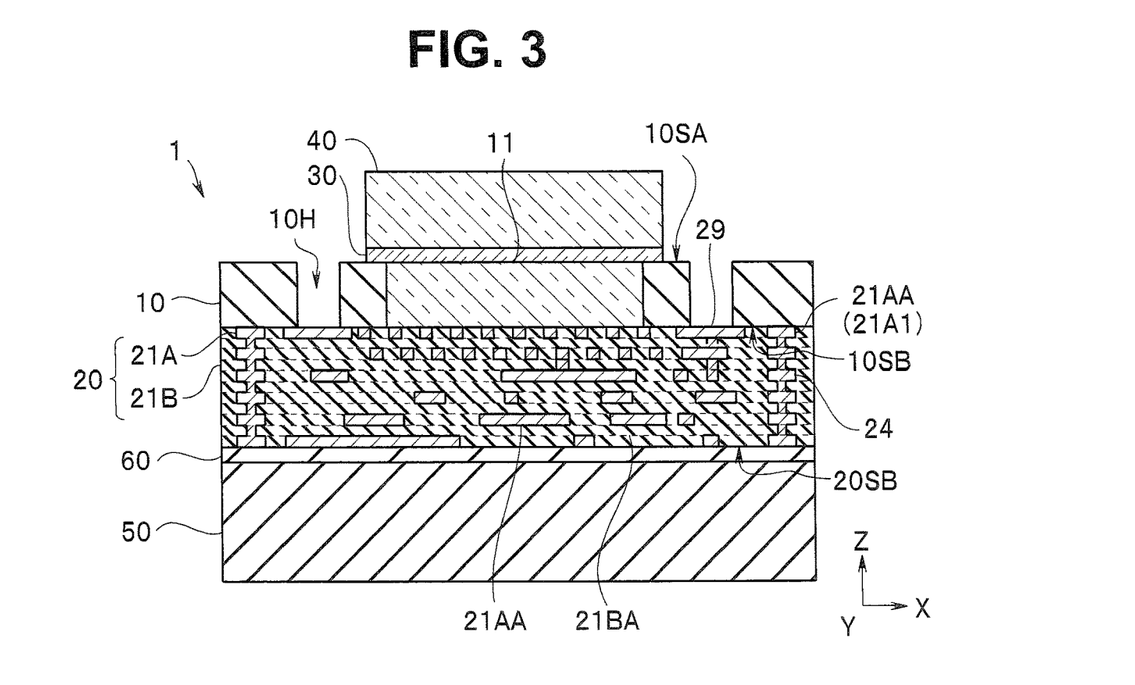
FIG. 3 is a cross-sectional view of the image pickup apparatus in the first embodiment, taken along line II-II in FIG. 2.

As shown in FIG. 1 to FIG. 3, an image pickup apparatus 1 in a first embodiment includes a silicon layer 10, a wire layer 20, an adhesive layer 30, a cover glass 40 that is a transparent member, a silicon substrate 50 that is a support substrate, and an adhesive layer 60. The adhesive layer 30 attaches the cover glass 40 to the silicon layer 10. The adhesive layer 60 attaches the silicon substrate 50 to the wire layer 20. For example, a thickness (Z-direction) of the silicon layer 10 is 3 µm to 8 µm, thicknesses of the wire layer 20, the adhesive layer 30 and the adhesive layer 60 are about 5 µm to 20 µm, and a thickness of the cover glass 40 is 150 µm to 5 mm.

Note that the drawings are schematic drawings and relations of thicknesses and widths of respective portions, ratios of thicknesses of individual portions, the number of laminations, and the like are different from reality. Even among the drawings, portions different from each other in relations and ratios of dimensions are contained in some cases. Further, for some components, illustrations and descriptions are omitted. For example, for a silicon oxide layer formed on a surface of the silicon layer 10 by oxidation treatment, neither illustration nor description is made. Further, the wire layer 20 having a multi-layer structure is simplistically illustrated.

On the silicon layer 10, a light receiving portion 11 including a CMOS and the like is formed by a semiconductor making technology. The wire layer 20 is disposed on a facing surface 10SB facing a light receiving surface 10SA that light received by the light receiving portion 11 of the silicon layer 10 enters. The cover glass 40 is attached to the light receiving surface 10SA of the silicon layer 10 so as to cover the light receiving portion 11. The adhesive layer 30 is composed of a transparent resin having a higher moisture resistance than a low dielectric constant material of insulating layers 21B, as exemplified by an epoxy resin and a silicone resin. Further, the transparent member may be composed of a resin or the like, if the material is a material having a high transmittance in a wavelength region of the light received by the light receiving portion 11.

The silicon substrate 50 is attached so as to cover a back surface 20SB of the wire layer 20, which is a surface on an opposite side of the silicon layer, through the adhesive layer 60. The silicon substrate 50 is a support wafer on which a semiconductor wafer (a silicon substrate as an image pickup device wafer) having the light receiving portion 11 formed is processed to the silicon layer 10 by performing polishing processing and thinning. The adhesive layer 60 may be the same resin as the adhesive layer 30, or may be an opaque resin.

The wire layer 20 is configured by a multi-layer wire in which a plurality of conductor layers 21A and a plurality of insulating layers 21B are laminated. The wire layer 20 configures a wiring circuit through which fine wires of the light receiving portions 11 and electrode pads 29 are connected. Note that conductors 21AA of the conductor layers 21A, in the wire layer 20, are connected to upper and lower conductors 21AA through conductors 21AA filled into through-holes of the insulating layers 21B. Further, insulators 21BA are disposed on side surfaces of the conductors 21AA of the conductor layers 21A. That is, the conductor layers 21A and the insulating layer 21B both contain the conductors 21AA and the insulators 21BA.

Furthermore, in the image pickup apparatus 1, the insulating layer 21B is composed of a material having a lower dielectric constant than silicon oxide, a so-called Low-k material.

The lower dielectric constant material is a material having a lower relative dielectric constant k than silicon oxide (k=4.0), and preferably should be a material having a relative dielectric constant k of 3.0 or lower. A lower limit of the relative dielectric constant k of the lower dielectric constant material, because of technological limitations, is 1.5 or higher, and preferably should be 2.0 or higher.

In the image pickup apparatus 1, the lower dielectric constant material of the insulating layer 21B is a porous carbon-doped silicon oxide film (SiOC). The porous SiOC is formed as a porous body having a structure with voids, and allows the relative dielectric constant k to be 2.7.

As the material of the insulating layer 21B, a fluorine-doped silicon oxide film (SiOF/FSG), a hydrogen-containing polysiloxane (HSQ) material, a methyl-containing polysiloxane (MSQ) material, an organic (polyimide, parylene, fluorine) material and the like can be used other than SiOC.

Note that only the insulators 21BA of some insulating layers, for example, insulating layers 21B close to the silicon layer 10 may be composed of the Low-k material.

Furthermore, as shown in FIG. 2 and the like, a frame-shaped guard ring 24 is formed along an outer edge on the wire layer 20. The guard ring 24 is formed when the wire layer 20 is disposed. The guard ring 24 is a moisture-proof wall that penetrates the wire layer 20, and blocks permeation of water into the insulator 21BA that is inside the guard ring 24 and that has the lower dielectric constant. Note that a part of the insulator 21BA exists also outside the guard ring 24 but the permeation of water into an interior of the guard ring 24 is prevented.

The image pickup apparatus 1 is a backside illumination type image pickup apparatus having a high sensitivity. The image pickup apparatus 1 is made through a step of bonding a semiconductor wafer (image pickup device wafer) on which many light receiving portions 11 and many wire layers 20 are disposed, to the silicon substrate (support wafer) 50, and performing a thinning process.

The cover glass 40 covers the light receiving portion 11 on the silicon layer 10. The cover glass 40, which has a sufficiently large thickness, blocks the permeation of water from a light receiving surface side. However, the light receiving surface 10SA has a region that is not covered with the cover glass 40. In the region of the silicon layer 10 that is not covered with the cover glass 40, pad openings 10H each of which is a through-hole having a bottom surface configured by an electrode pad 29 to connect the conductor 21AA of the wire layer 20 and an external wire (not illustrated), which is a conducting wire of a signal cable, exist.

The pad opening 10H is formed by a wet etching using an alkaline solution of KOH, TMAH or the like, or a dry etching using a fluorine-containing gas of $CF_4$, $CHF_3$, $C_2F_6$ or the like.

Furthermore, the electrode pad 29 is configured by the conductor 21AA of an uppermost conductor layer 21A1 of the wire layer 20 that is in contact with the silicon layer 10.

The conductor 21AA is composed of copper, for example. The electrode pad 29 is also an etching-stop layer when the pad opening 10H is formed.

Planar-view dimensions of the electrode pad 29 are larger than planar-view dimensions of the pad opening 10H, and an outer periphery portion of the electrode pad 29 is in contact with the silicon layer 10 over a whole periphery.

In the pad opening 10H, the bottom surface is configured by the electrode pad 29 composed of a metal material such as copper, which has a good moisture resistance. Therefore, the image pickup apparatus 1 has no possibility that water permeates the insulator 21BA of the wire layer 20 through the pad opening 10H.

In the image pickup apparatus 1, intrusion of moisture from side surfaces into the insulator 21BA that is of the wire layer 20 and that has the lower dielectric constant is prevented by the guard ring 24. Intrusion of moisture from a back surface is prevented by the silicon substrate 50 that is a protective portion. Intrusion of moisture from the pad opening 10H is prevented by the electrode pad 29.

Therefore, in the image pickup apparatus 1, moisture does not intrude into the insulator having the lower dielectric constant, and the image pickup apparatus 1 has a high reliability.

For example, even after the image pickup apparatus 1 was left for 1000 hours under a hot and humid environment of 85° C. and a humidity of 85%, characteristics of the image pickup apparatus 1 did not deteriorate.

Modifications of First Embodiment

Next, image pickup apparatus 1A to 1E in Modifications 1 to 5 of the first embodiment will be described. The image pickup apparatus 1A to 1E are similar to the image pickup apparatus 1 in the first embodiment, and have the function of the image pickup apparatus 1. Therefore, identical reference characters are assigned to components having identical functions, and the descriptions are omitted.

<Modification 1>

Figure 4:
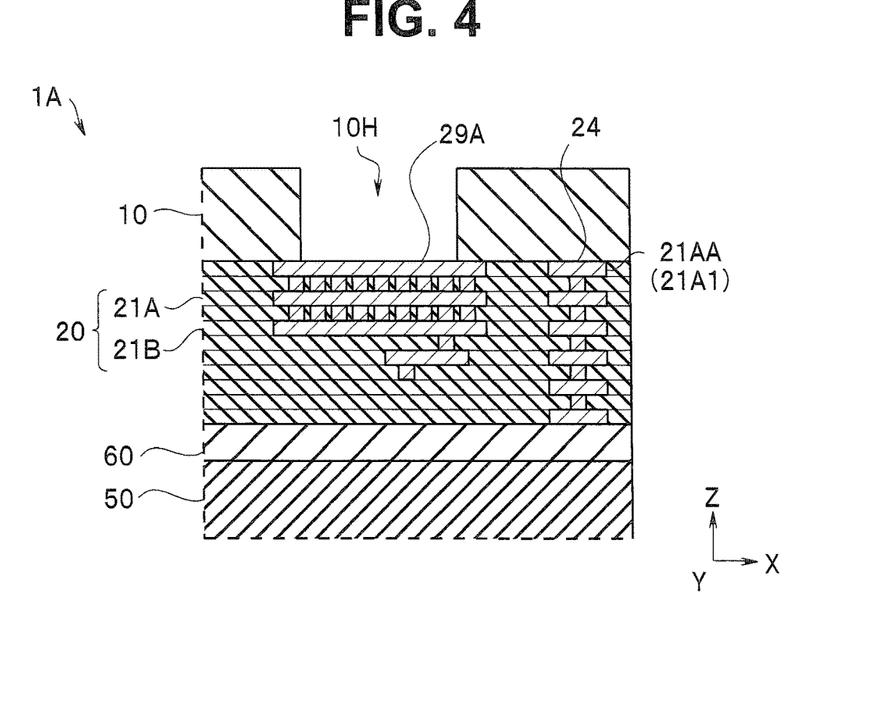
FIG. 4 is a partial cross-sectional view of an image pickup apparatus in Modification 1 of the first embodiment.

As shown in FIG. 4, in the image pickup apparatus 1A in Modification 1, an electrode pad 29A is configured by a plurality of conductor layers 21A of the wire layer 20.

The thickness of the copper conductor layer 21A of the wire layer 20 is 0.1 μm to 0.8 μm, and is not large. Therefore, in a case where the electrode pad 29 is configured by only the conductor 21AA of the uppermost conductor layer 21A1, a connection with the external wire can be difficult, or the moisture resistance can deteriorate when the external wire is connected.

On the other hand, in the image pickup apparatus 1A in which the electrode pad 29A is configured by a plurality of conductor layers 21A, for example, by three to ten conductor layers 21A, the connection with the external wire is easier than in the image pickup apparatus 1, and the moisture resistance is high.

<Modification 2>

Figure 5:
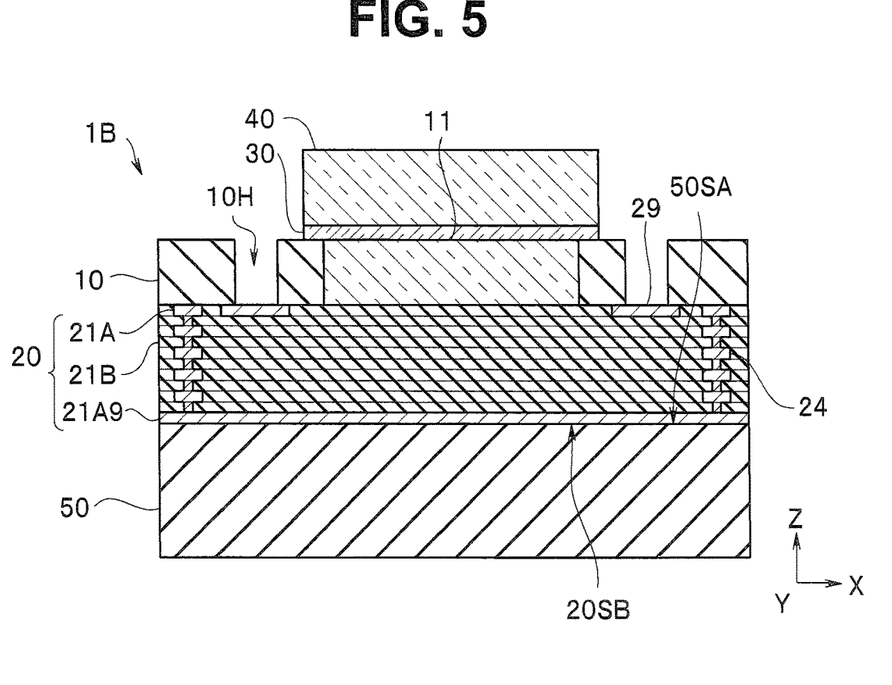
FIG. 5 is a cross-sectional view of an image pickup apparatus in Modification 2 of the first embodiment.

As shown in FIG. 5, in the image pickup apparatus 1B in Modification 2, the silicon substrate 50 is directly bonded to the wire layer 20, without interposing another member.

For performing the direct bonding, the back surface 20SB of the wire layer 20 is processed so as to have a high flatness ttv, similarly to a front surface 50SA of the silicon substrate 50. For example, the back surface 20SB of the wire layer 20 and the front surface 50SA of the silicon substrate 50 both have a flatness ttv (total thickness variation) of 1 μm or less, and preferably should have a high flatness of 0.5 μm or less. The flatness ttv is a difference between the maximum and the minimum of thickness-directional heights that are measured over the whole surface with respect to the bonding surface as a reference plane. Further, for easily obtaining a high flatness, it is preferable that the back surface 20SB of the wire layer 20 is configured by only a conductor layer 21A9, the whole surface of which is covered with the conductor, as shown in FIG. 5.

As a method for the direct bonding, for example, after flattening processing of the back surface 20SB of the wire layer 20 by a CMP method, a normal-temperature bonding method of putting the two on each other in a state where the bonding surfaces of the two are irradiated with an ion beam in high vacuum and oxide films and adsorbates on the surfaces are removed, is used.

Note that the method for the direct bonding is not limited to the above-described normal-temperature bonding method in vacuum and a diffusion bonding method of performing heat treatment after putting the two on each other at normal temperature in the atmosphere, or the like may be used.

The image pickup apparatus 1B does not include the adhesive layer 60, and therefore has a further higher reliability than the image pickup apparatus 1.

<Modification 3>

Figure 6:
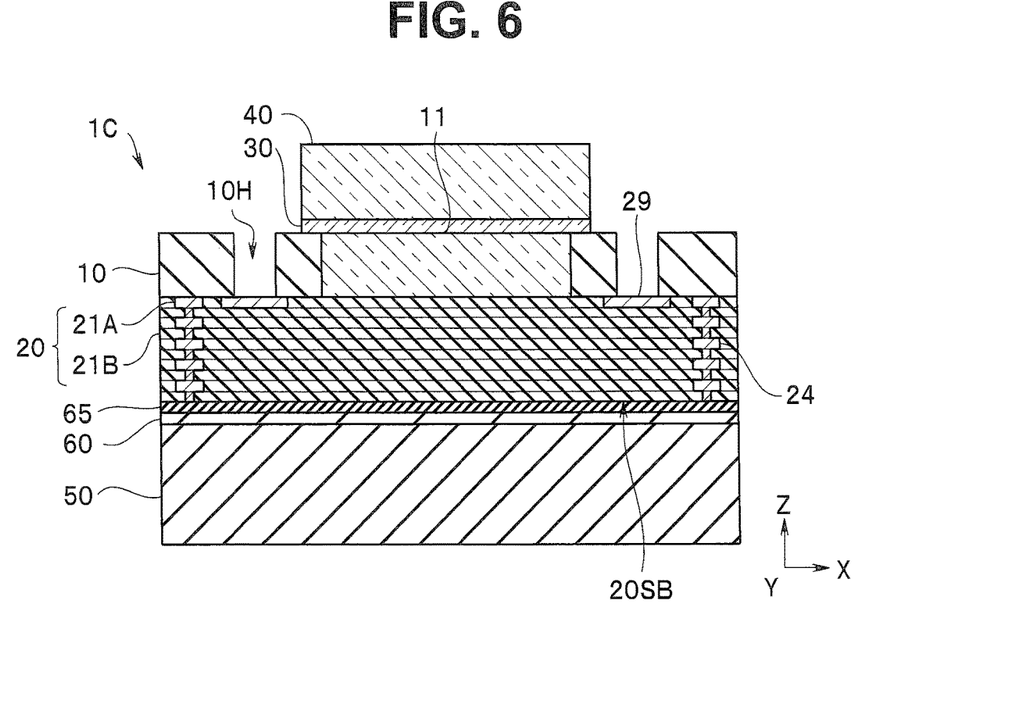
FIG. 6 is a cross-sectional view of an image pickup apparatus in Modification 3 of the first embodiment.

As shown in FIG. 6, in the image pickup apparatus 1C in Modification 3, a protective film 65 composed of an inorganic material is disposed between the adhesive layer 60 and the back surface 20SB of the wire layer 20.

The protective film 65 is composed of a material having a low moisture permeability, as exemplified by silicon oxide and silicon nitride, and has a film thickness of 0.3 μm to 5 μm.

Since the back surface 20SB of the wire layer 20 is covered with the protective film 65 that is composed of a resin and that has a lower moisture permeability than the adhesive layer 60, the image pickup apparatus 1C has a further higher reliability than the image pickup apparatus 1.

Note that the wire layer 20 on which the protective film 65 is disposed may be directly bonded to the silicon substrate 50 without interposing the adhesive layer 60.

<Modification 4>

Figure 7:
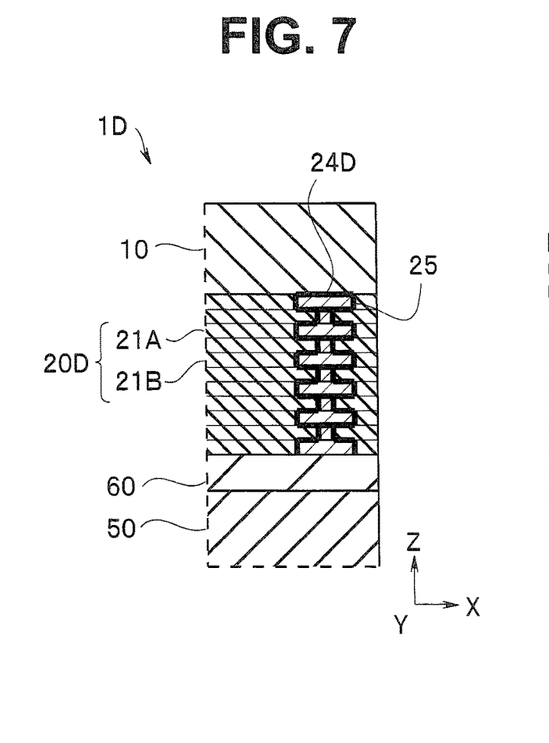
FIG. 7 is a partial cross-sectional view of an image pickup apparatus in Modification 4 of the first embodiment.

As shown in FIG. 7, in the image pickup apparatus 1D in Modification 4, a surface of a guard ring 24D of the wire layer 20 is covered with an over coat layer 25 composed of silicon oxide.

As already described, the guard ring is formed using the copper that is the conductor 21AA of the conductor layer 21A at the time of making the wire layer 20. Copper is a metal having a good moisture permeability, but can corrode by the permeation of water because corrosion resistance is not high. The surface of the guard ring 24D is covered with the over coat layer 25 composed of silicon oxide having a high corrosion resistance. Therefore, the image pickup apparatus 1D has a higher reliability than the image pickup apparatus 1. It is preferable that the material of the over coat layer 25 is a material having a high corrosion resistance, for example, an oxide such as silicon oxide or a nitride such as silicon nitride.

Figure 8:
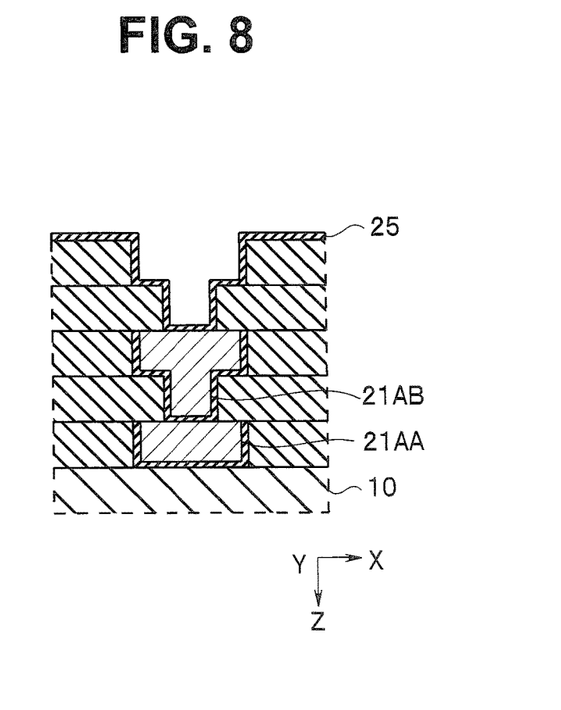
FIG. 8 is a partial cross-sectional view for describing a production method for the image pickup apparatus in Modification 4 of the first embodiment.

As shown in FIG. 8, using a sputtering method or a CVD method, the over coat layer 25 is deposited on an inner surface of a hole formed for the guard ring, at the time of making a wire layer 20D. Then, copper (21AB) is filled into an interior of the hole by a known damascene method, and thereby, the guard ring 24D is made. In FIG. 8, a dual damascene method is shown as an example, but a single damascene method may be adopted.

<Modification 5>

Figure 9:
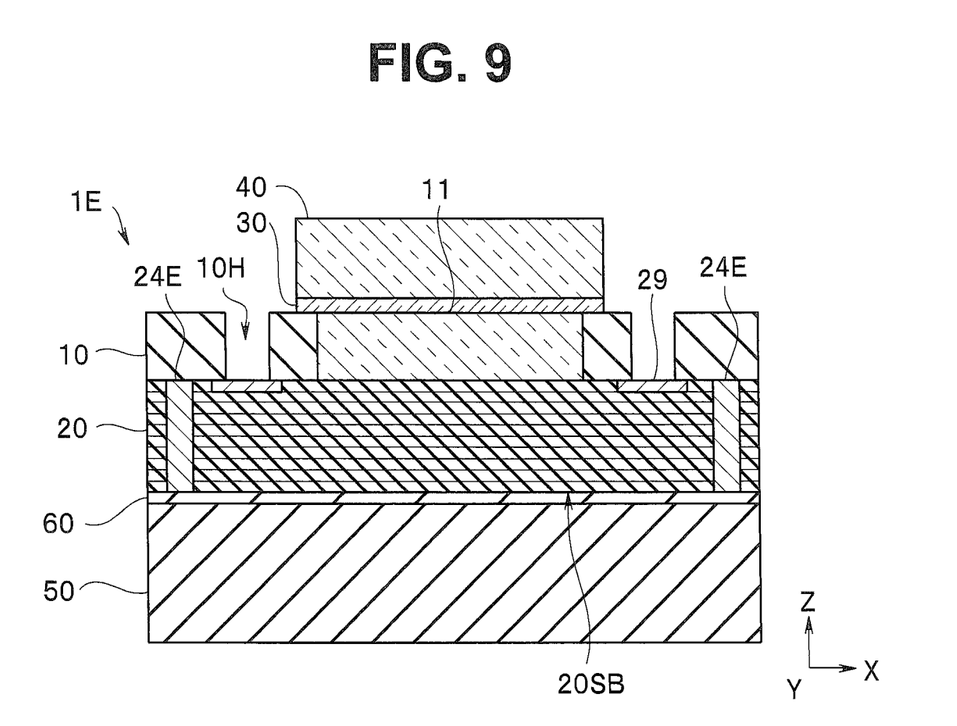
FIG. 9 is a cross-sectional view of an image pickup apparatus in Modification 5 of the first embodiment.

As shown in FIG. 9, a guard ring 24E of the image pickup apparatus 1E in Modification 5 is configured by a metal covering a trench that passes through the wire layer 20.

That is, in the case where the guard ring is not formed in the wire layer 20, a frame-shaped trench is formed by an etching from a back surface 20SB side of the wire layer 20, before the thinning of the silicon wafer is performed. The trench passes through the wire layer 20, and has a bottom surface that is configured by the silicon layer 10. Then, a metal material, for example, copper is filled into an interior of the trench, and thereby, the guard ring 24E is made. The material to be filled into the interior of the trench may be an inorganic material such as silicon oxide and silicon nitride, if the material has a higher moisture resistance than the Low-k material.

The image pickup apparatus 1E has a high reliability similarly to the image pickup apparatus 1, because of including the guard ring 24E.

Note that only an inner wall of the trench may be covered with an inorganic material having a higher moisture resistance than the Low-k material. Moreover, a metal material such as copper may be filled into the interior of the trench after the inner wall of the trench is covered with a film composed of an inorganic material such as silicon oxide that is the same as the material of the over coat layer 25. Conversely, the inorganic material such as silicon oxide may be filled into the interior of the trench after the inner wall is covered with the metal material.

Note that side surfaces of the image pickup apparatus 1 may be covered with a protective layer composed of at least one of an insulating material and a metal material, instead of the guard ring 24, for blocking the permeation of water from the side surfaces. Further, an O-ring may be fit to the trench.

Second Embodiment

Figure 10:
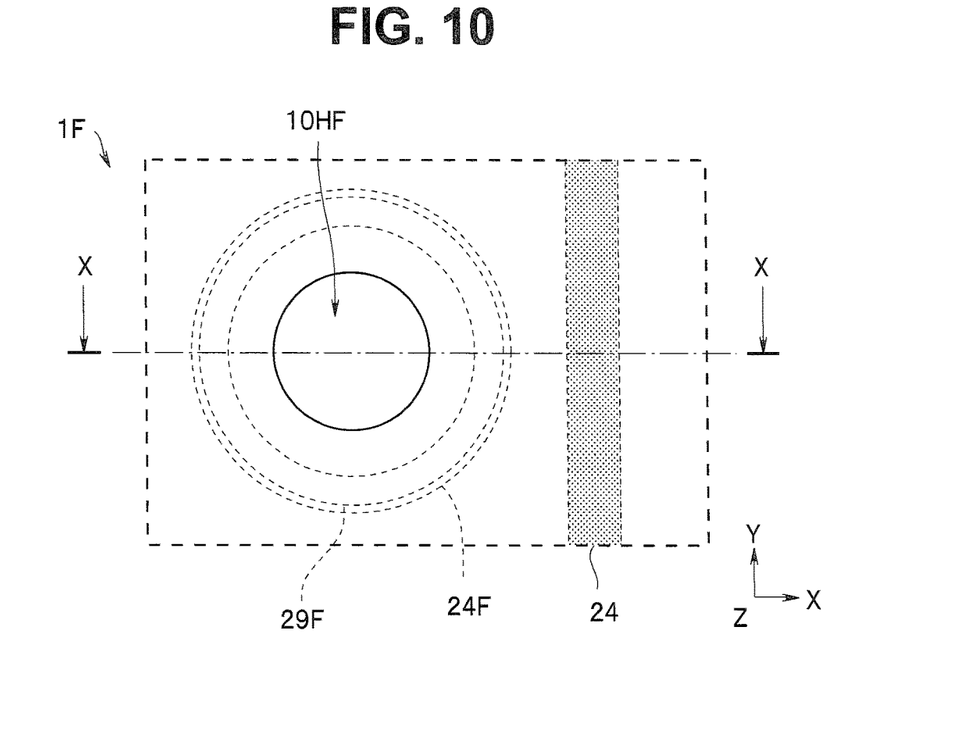
FIG. 10 is a partial plan view of an image pickup apparatus in a second embodiment.
Figure 11:
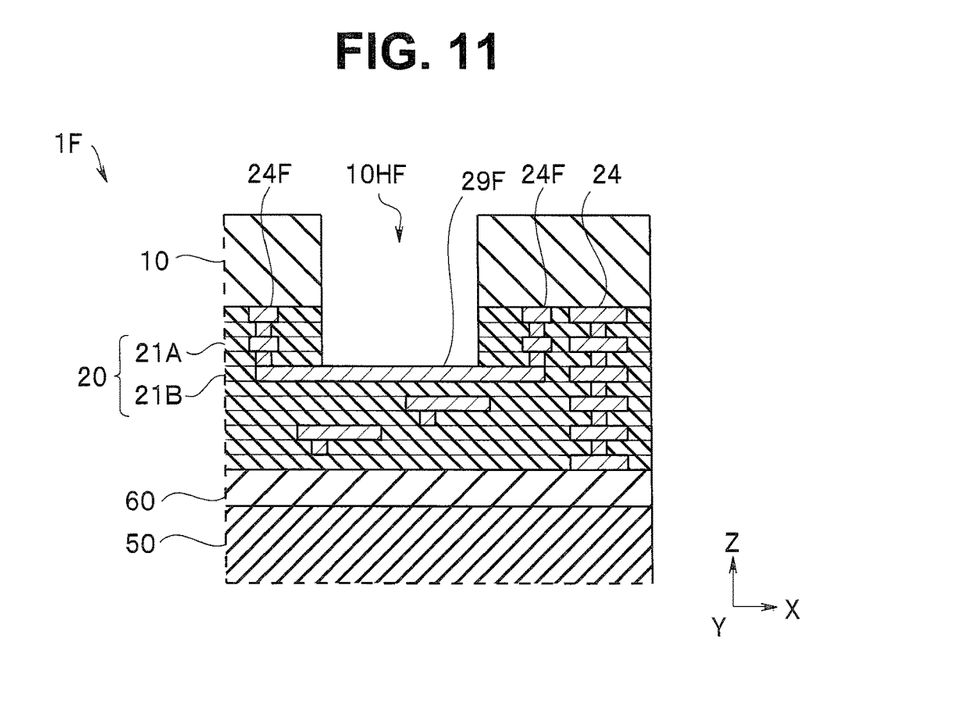
FIG. 11 is a partial cross-sectional view of the image pickup apparatus in the second embodiment.

Next, an image pickup apparatus 1F in a second embodiment will be described. The image pickup apparatus 1F is similar to the image pickup apparatus 1 in the first embodiment, and has the function of the image pickup apparatus 1. Therefore, identical reference characters are assigned to components having identical functions, and the descriptions are omitted.

As shown in FIG. 10 and FIG. 11, in the image pickup apparatus 1F, a pad opening 10HF that is a through-hole having a bottom surface configured by an electrode pad 29F passes through not only the silicon layer 10 but also a part of the wire layer 20. Therefore, the insulating layer 21B is exposed to a wall surface at a lower portion of the pad opening 10HF.

However, a pad guard ring 24F that surrounds the pad opening 10HF in the wire layer is formed in the wire layer 20. Furthermore, an outer periphery portion of the electrode pad 29F is in contact with the pad guard ring 24F over a whole periphery.

In the image pickup apparatus 1F, the permeation of water from the pad opening 10HF is prevented by the pad guard ring 24F.

Note that by adding the configurations of the image pickup apparatuses 1A to 1E in Modifications 1 to 5 of the first embodiment, the effects of the respective modifications can be obtained also in the image pickup apparatus 1F.

Third Embodiment

Next, an endoscope system 9 including an endoscope 2 in a third embodiment will be described.

Figure 12:
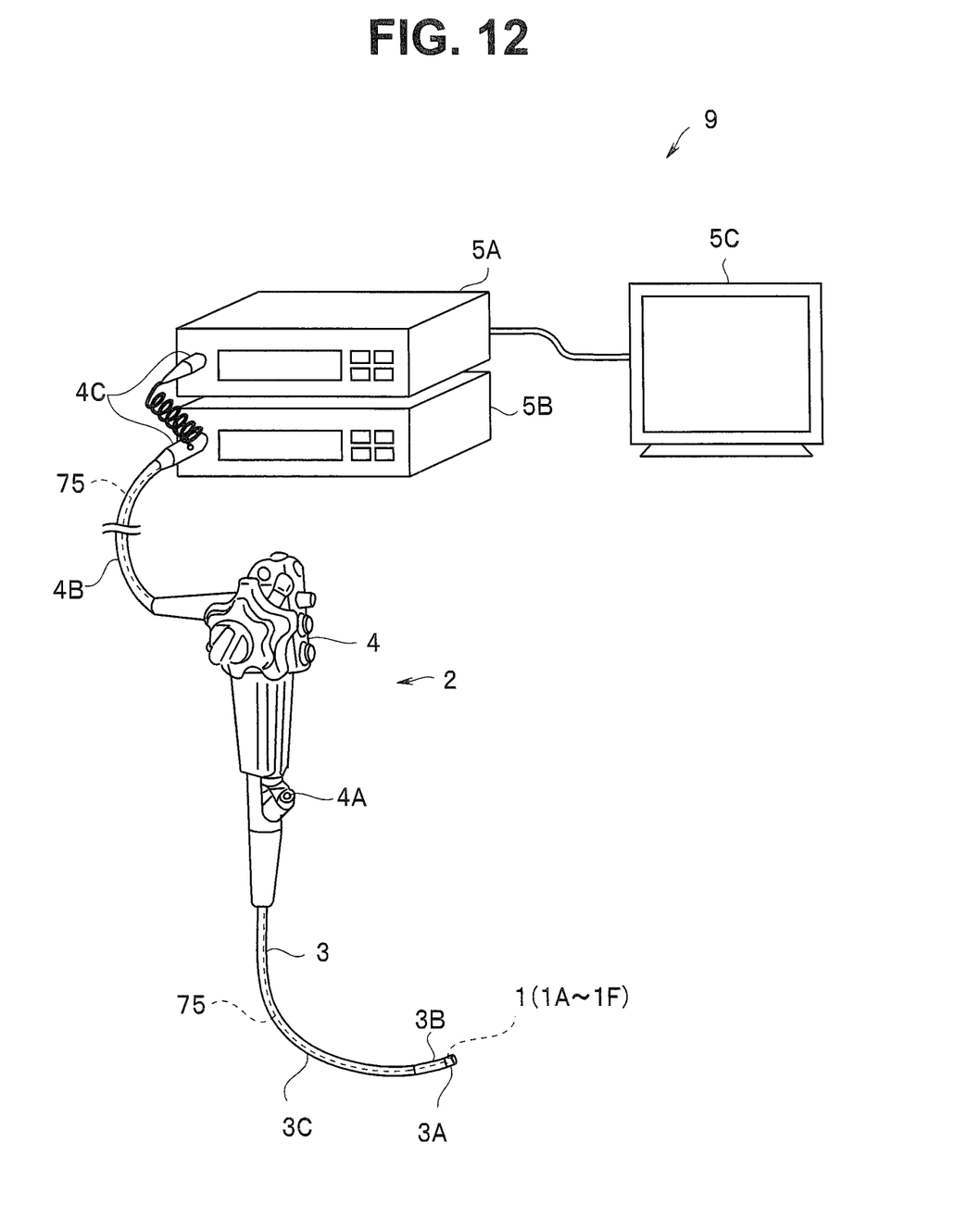
FIG. 12 is a perspective view of an endoscope system including an endoscope in a third embodiment.

As shown in FIG. 12, the endoscope system 9 includes the endoscope 2, a processor 5A, a light source apparatus 5B and a monitor 5C. The endoscope 2, an insertion portion 3 of which is inserted into a body cavity of a subject, pickups an internal body image of the subject and outputs an image pickup signal. That is, the endoscope 2 includes one of the image pickup apparatuses 1, 1A to 1F, at a distal end portion of the insertion portion 3.

On a proximal end side of the insertion portion 3 of the endoscope 2, an operation portion 4 provided with various buttons through which the endoscope 2 is operated is disposed. The operation portion 4 includes a treatment-instrument insertion opening 4A of a channel that allows a treatment instrument such as a body forceps, an electric knife and an examination probe to be inserted into the body cavity of the subject.

The insertion portion 3 is configured by a distal end portion 3A at which the image pickup apparatus 1 is disposed, a bending portion 3B that is continuously provided on a proximal end side of the distal end portion 3A and that is bendable, and a flexible tube portion 3C that is continuously provided on a proximal end side of the bending portion 3B. The bending portion 3B is bent by an operation with the operation portion 4.

A universal cord 4B disposed on a proximal end portion side of the operation portion 4 allows insertion of a signal cable 75 connected to the image pickup apparatus 1 at the distal end portion 3A.

The universal cord 4B is connected to the processor 5A and the light source apparatus 5B through a connector 4C. The processor 5A controls a whole of the endoscope system 9, and performs signal processing of the image pickup signal outputted by the image pickup apparatus 1, to output an image signal. The monitor 5C displays the image signal outputted by the processor 5A.

The light source apparatus 5B includes a white LED, for example. White light emitted by the light source apparatus 5B is guided to an illuminance optical system (not illustrated) at the distal end portion 3A, by a light guide (not illustrated) allowing insertion of the universal cord 4B, and illuminates an object.

The endoscope 2 has a high reliability, because of including one of the image pickup apparatus 1, 1A to 1F, which has a high reliability, at the distal end portion of the insertion portion.

The present invention is not limited to the above described embodiments, the modifications and the like, and various alterations, variations, combinations and others can be made in a range without changing the spirit of the present invention.

What is claimed is:

1. An image pickup apparatus comprising:
   a silicon layer that includes a light receiving surface and a facing surface, the light receiving surface being a surface that light received by a light receiving portion enters;
   a wire layer that is disposed on the facing surface, the wire layer including a plurality of conductor layers and a plurality of insulating layers, each of the plurality of conductor layers containing a conductor that is connected to the light receiving portion, each of the plurality of insulating layers containing an insulator that has a lower dielectric constant than silicon oxide;
   a transparent member that covers the light receiving portion on the light receiving surface of the silicon layer; and a protective portion that covers a back surface of the wire layer, the back surface being a surface on an opposite side of the silicon layer, wherein a guard ring is formed along an outer edge on the wire layer, a through-hole is provided in a region of the silicon layer that is not covered with the transparent member, the through-hole having a bottom surface that is configured by an electrode pad, the electrode pad being configured by at least one of the conductors of the conductor layers and having an outer periphery portion in contact with the silicon layer over a whole periphery, and the insulators having the lower dielectric constant of the insulating layers are not exposed to an inner surface of the through-hole.

2. The image pickup apparatus according to claim 1, wherein the electrode pad is configured by two or more conductor layers of the wire layer.

3. The image pickup apparatus according to claim 1, wherein the protective portion is a silicon substrate.

4. The image pickup apparatus according to claim 3, wherein the silicon substrate is attached to the back surface of the wire layer through an adhesive layer.

5. The image pickup apparatus according to claim 4, wherein a protective film composed of an inorganic material is disposed between the adhesive layer and the back surface of the wire layer.

6. The image pickup apparatus according to claim 1, wherein the guard ring composed of a metal is covered with an oxide or a nitride.

7. The image pickup apparatus according to claim 1, wherein the guard ring is composed of an inorganic material filled into a trench that passes through the wire layer.

8. The image pickup apparatus according to claim 7, wherein the inorganic material is a metal.

9. An endoscope comprising the image pickup apparatus according to claim 1, at a distal end portion of an insertion portion.

* * * * *